United States Patent [19]

Hanson

[11] 4,441,366

[45] Apr. 10, 1984

[54] FLEXURE WITH ELECTRICAL CONDUCTOR

[75] Inventor: Richard A. Hanson, Woodinville, Wash.

[73] Assignee: Sundstrand Data Control, Inc., Redmond, Wash.

[21] Appl. No.: 283,341

[22] Filed: Jul. 14, 1981

[51] Int. Cl.$^3$ .............................................. G01P 15/13
[52] U.S. Cl. ................................. 73/517 B; 174/70 R
[58] Field of Search ............. 73/497, 514, 515, 516 R, 73/517 R, 517 B; 174/70 R; 200/61.51

[56] References Cited

U.S. PATENT DOCUMENTS

| | | | |
|---|---|---|---|
| 3,020,767 | 2/1962 | Kistler | 73/497 |
| 3,229,530 | 1/1966 | Wilcox et al. | 73/517 B |
| 3,331,253 | 7/1967 | Morris | 73/517 B |
| 3,339,419 | 9/1967 | Wilcox | 73/517 B |
| 3,513,711 | 5/1970 | Rogall et al. | 73/517 B |
| 3,702,073 | 11/1972 | Jacobs | 73/517 B |
| 4,182,187 | 1/1980 | Hanson | 73/517 B |
| 4,250,757 | 2/1981 | Hanson | 73/517 B |

*Primary Examiner*—James J. Gill
*Attorney, Agent, or Firm*—Wood, Dalton, Phillips, Mason & Rowe

[57] ABSTRACT

A flexure in a transducer such as an inertial guidance accelerometer for suspending a force sensitive element to a mounting base includes a reduced thickness central portion and a pair of relatively thick ribs disposed on opposite sides of the central portion. An electrically conductive coating is disposed on at least one face of the central portion to provide electrical connections to components located on the element. The reduced thickness of the central portion minimizes errors caused by stresses in the interface between the conductive coating and the element and the relatively thick ribs provide a desired strength and spring rate for the element suspension.

33 Claims, 5 Drawing Figures

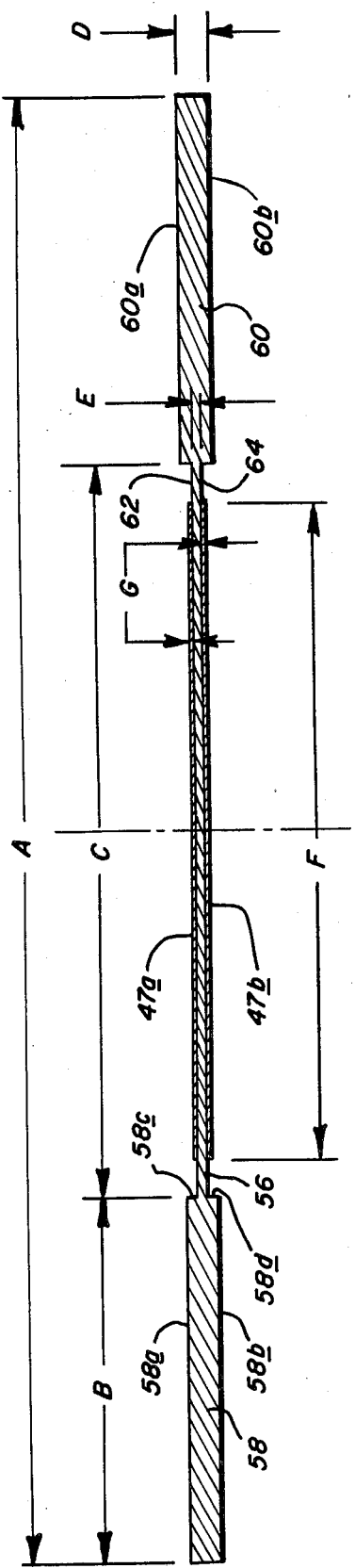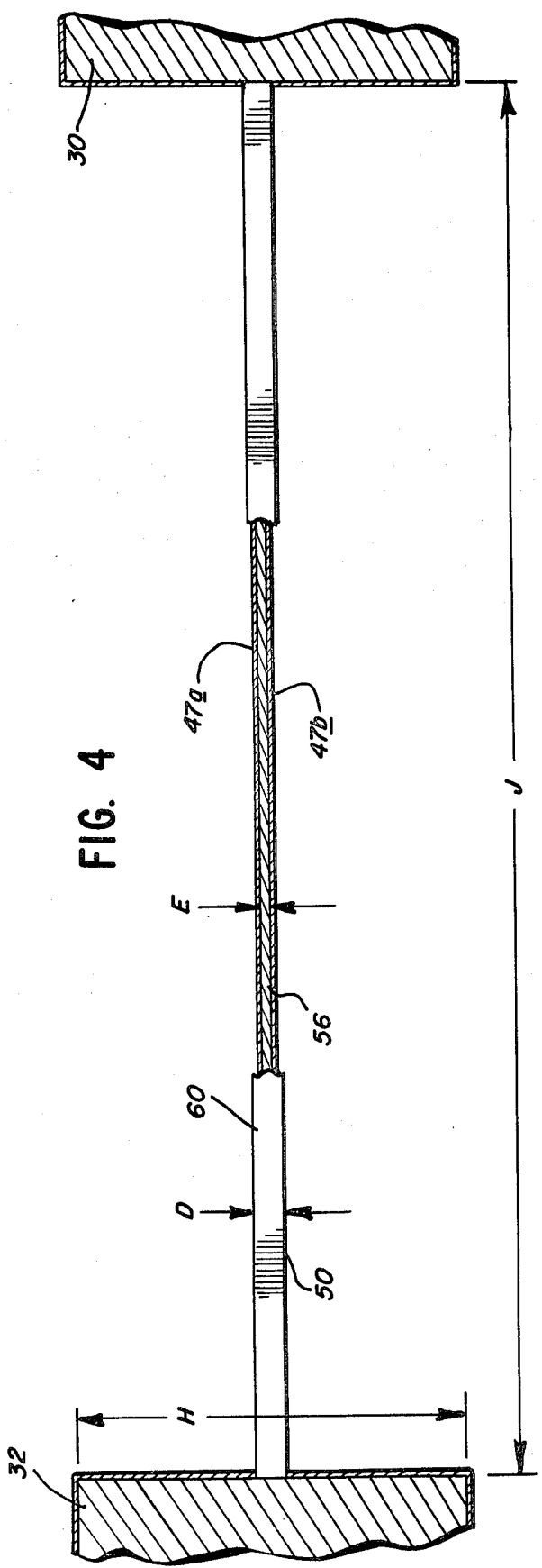

FLEXURE WITH ELECTRICAL CONDUCTOR

BACKGROUND OF THE INVENTION

This invention relates to the field of force sensing transducers, such as accelerometers, and, more particularly, to a flexure for hingedly or translationally securing a force sensing element to a mounting base.

In a prior accelerometer, such as that disclosed in Jacobs U.S. Pat. No. 3,702,073, a force sensing element is secured to a mounting base or ring by means of a flexure which allows the element to move in response to small forces relative to the base. In such an accelerometer, the flexure may have a bifilar construction consisting of a pair of thin planar members.

In order to provide electrical connections to components located on the sensing element, flexible leads between the ring and sensing element may be used, or a thin film of conductive material may be deposited directly on the flexure or on a nonconductive coating on the flexure if the flexure itself is electrically conductive. When such materials are deposited on the flexure, stresses are set up in the flexure due to the differing temperature coefficients of the flexure and conductive materials, or by the deposition process itself. These stresses in turn result in forces which attempt to deflect the sensing element from a neutral position. In servoloop transducers which apply a restoring force to maintain the sensing element in the neutral position, a bias error is developed as a result of these stresses. In open-loop transducers wherein the amount of deflection of the sensing element is measured, a bias error is also produced.

In those transducers which utilize conductive coatings, an effort is made to cancel out the film stresses by depositing the films equally on the upper and lower faces of the flexure sections. While this construction reduces errors to some degrees, it requires a precise balancing during the deposition process so that the film thickness is equal on both sides of the flexure section. Moreover, this balance is dependent upon film stress stability with respect to time, and is also dependent upon other factors such as ambient temperature, material purity and surface contamination.

In general, in prior transducers it has been found desirable to utilize the thinnest possible flexure consonant with strength and elasticity requirements for proper operation, so that stress effects leading to bias errors are minimized. However, it has been found that the spring rate, whether angular or linear, provided by a flexure is proportional to the cube of the thickness "t" thereof, while the bending moment of the flexure due to stress caused by deposition of the conductive strips is only proportional to t. For example, if the thickness of the flexure is reduced by 30 percent such that the angular spring rate provided thereby is changed from 20g/radian to 7g/radian, the error moment due to stress effects in the conductive plating is reduced by a factor of only 1.42. Hence, it can be seen that the lower limit of the range of acceptable spring rates provided by a conventional flexure will be reached well before the error moment is reduced to an insignificant value. Consequently, for these types of flexures, tradeoffs must be made between obtaining the desired spring rate and flexure strength and minimizing stress effects which lead to errors.

SUMMARY OF THE INVENTION

It is therefore an object of the invention to provide a flexure structure for connecting a force sensing element to a mounting base in a force sensing transducer wherein the flexure includes a portion extending between the force sensing element and the mounting base having a surface for receiving an electrically conductive coating and a rib portion having a thickness greater than the thickness of the first portion extending between the force sensing element and the mounting base.

Also in accordance with the present invention, a flexure, for example, for hingedly mounting a force sensing element to a mounting base in a force sensing transducer may have a bifilar construction wherein each of a pair of flexure sections has a thin central portion and a pair of relatively thick ribs on either side of each central portion extending between the element and the mounting ring. A layer of conductive material is located on the upper and lower faces of each section within the central portion and between the ribs. In addition, it is desirable to have the conductive material located on each face such that it is equidistant from the neutral bending axis of the flexure.

By locating the conductive material on a relatively thin central portion, the bending moments caused by stresses in the conductive film are minimized, which in turn reduces bias errors by a significant degree. At the same time, the relatively thick ribs provide adequate strength and a suitable spring rate for proper operation of the transducer. A related approach to providing the desired flexure characteristics is disclosed in the copending applications Hanson Ser. Nos. 283,340, filed July 14, 1981, and Hanson and Atherton 283,129, filed July 14, 1981 assigned to the assignee of this application.

BRIEF DESCRIPTION OF THE DRAWINGS

FIG. 3 is a sectional view taken along line 3—3 of FIG. 2;

FIG. 4 is an elevational view, partly in section, taken along line 4—4 of FIG. 2.

DETAILED DESCRIPTION OF THE INVENTION

Figure 1:
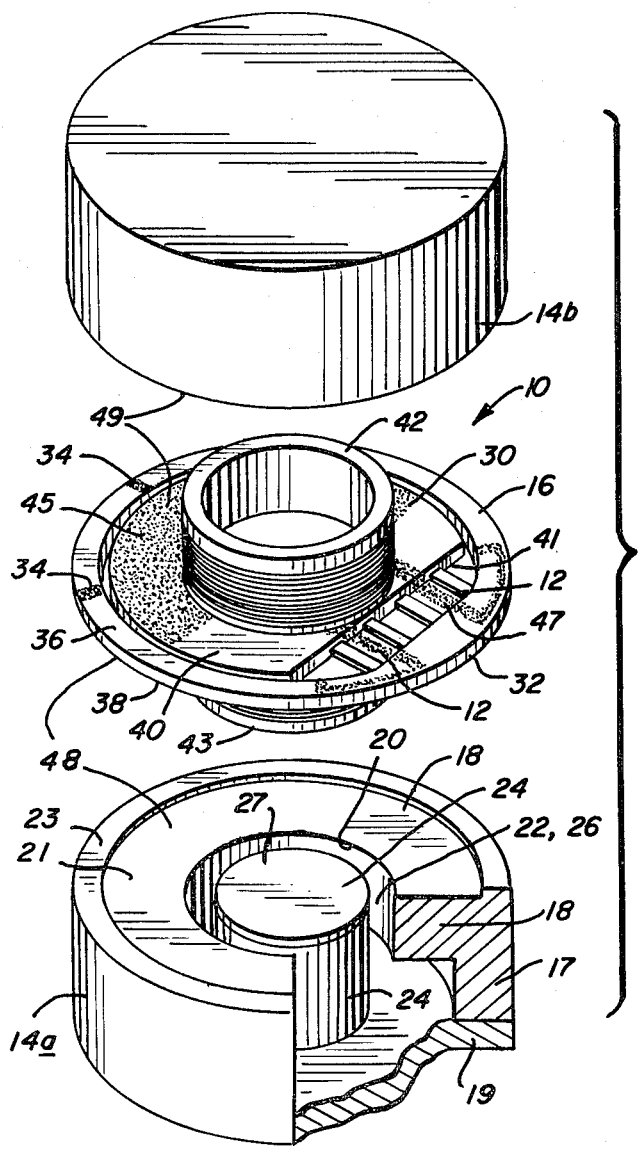
FIG. 1 is an exploded perspective view, partially in section, of an accelerometer incorporating the flexure of the present invention.

Referring to FIG. 1, there is illustrated a force transducer in the form of a servoed accelerometer 10 which includes a flexure 12 according to the present invention. The accelerometer 10 is of the type disclosed in Jacobs U.S. Pat. No. 3,702,073, although the invention may be used in other force sensing transducers utilizing angular or linear motion of a force sensitive element.

The accelerometer 10 consists of a pair of cylindrical body members 14a, 14b and a proof mass assembly 16 secured therebetween.

The body members 14a, 14b are substantially identical and, hence, only the body member 14a will be described. The body member 14a includes a cylindrical body wall 17 having an inwardly extending rib 18 constituting a magnetic pole piece and includes a base portion 19. The pole piece 18 has a cylindrical inner wall 20 defining a recess 22. Secured to the plate 19 within the recess 22 is a cylindrical permanent magnet 24 which has an outer circumferential surface spaced from the inner cylindrical wall 20 to define an annular gap 26 therebetween.

The proof mass assembly 16 includes a force sensitive member or paddle 30 which is hingedly mounted by means of the flexure 12 to a mounting base or ring 32.

In the accelerometer shown in the figures, the flexure 12 allows the paddle 30 to move arcuately relative to the mounting ring 32. However, it should be understood that the flexure 12 could be used in a transducer utilizing linear motion of the sensing element along the axis of the transducer 10.

Secured to upper and lower faces 40, 41 of the paddle are a pair of force restoring, or torquer coils 42, 43, respectively. The torquer coils 42, 43 are wound on bobbins which fit within the annular gap 26 formed in each of the body members 14a, 14b when the various parts of the accelerometer 10 are assembled.

Deposited on the upper face 40 of the paddle 30 is a layer of conductive material 45. A similar layer of conductive material is deposited on the lower face 41 of the paddle 30. These electrically conductive layers form a pair of capacitor plates which interact with a face 21 of the pole piece 18 and a corresponding face of the pole piece of body member 15b, in a manner to be hereinafter described.

Three mounting pads 34 (one of which is not shown in the figures) are disposed on an upper surface 36 of the mounting ring 32. Three additional mounting pads are located axially opposite the mounting pads 34 on a lower surface 38 of the ring 32.

The mounting ring 32 is secured between the body members 14a, 14b such that a lip 23 of the cylindrical body wall 17 and a corresponding lip on the body member 14b bear against the mounting pads, and the torquer coils 42, 43 are received within the annular gap 26 and a corresponding annular gap in the body member 14b, respectively.

A pair of variable capacitors 48, 49 are formed within the accelerometer 10, one of which consists of the face 21 and the coating on the lower surface 38, and the other of which consists of a face corresponding to the face 21 of the pole piece of the body member 14b and the coating 45 on the upper surface 36 of the paddle 30.

The conductive layers on the upper face 40 and the lower face 41 and the torquer coils 42, 43 are coupled to external circuitry by means of four conductive strips 47a–d which extend to the ring 32 across the flexure 12. The electrical connections to external circuitry are made from the ring 32 through four connector pins (not shown) located in the body walls of the body members 14a, 14b.

When the accelerometer 10 is subjected to acceleration along its axis, the paddle 30 moves relative to the ring 32 and the body members 14a, 14b, in turn causing a change in the capacity of the capacitors 48, 49. The change in capacity is detected by a servo-loop circuit (not shown), which in turn couples a signal proportional to the change in capacity to the torquer coils 42, 43. The resulting magnetic field set up by the torquer coils 42, 43 interacts with the magnetic field established by the permanent magnets in the body members 14a, 14b, to oppose the displacement of the paddle 30. The current required by the torquer coils 42, 43 to maintain the paddle 30 in a neutral position represents the acceleration force to which the accelerometer is subjected.

For a further description of the accelerometer 10, reference should be made to Jacobs U.S. Pat. No. 3,702,073, the disclosure of which is incorporated herein.

Figure 2:
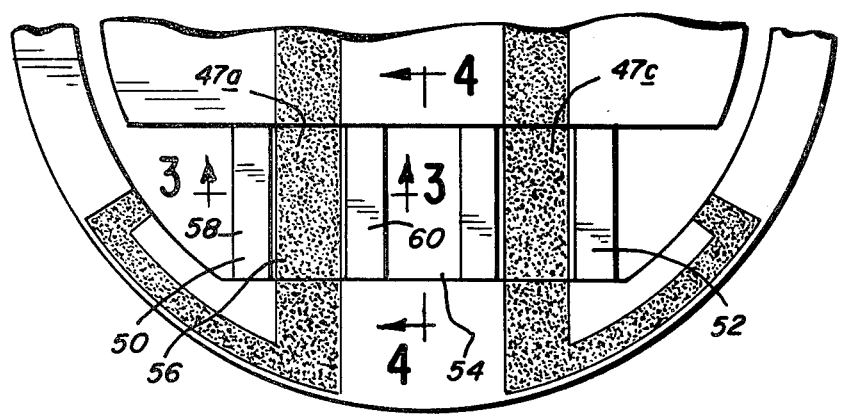
FIG. 2 is an enlarged plan view of a portion of the proof mass assembly shown in FIG. 1.

Referring now to FIGS. 2–4, the flexure 12 of the present invention is illustrated in detail. The flexure configuration and construction is such as to minimize stress effects occurring in the interface between the conductive strips 47 and the flexure 12, which in turn cause an error to appear at the output of the indicating circuitry.

As seen more particularly in FIG. 2, the flexure construction consists, in the preferred embodiment, of a ribbed bifilar cantilever structure having a pair of sections 50, 52 separated by an aperture 54. The paddle 30, mounting base 32 and flexure 12 may be a single integral piece of fused quartz which is etched or otherwise processed to the desired dimensions and configuration.

The flexure 12 could alternatively be formed from electrically conductive material, in which case an electrically nonconductive coating is deposited on the flexure 12 before the conductive strips 47 are deposited.

As seen more particularly in FIG. 3 illustrating the preferred embodiments of the invention, each of the sections 50, 52 includes a pair of channels extending between the mounting base 32 and the paddle 30 defining a thin central portion 56 and a pair of relatively thick ribs 58, 60 located on either side of the central portion 56. In the preferred embodiment, the channels are of even depth such that the thickness of the central portion 56 is less than one-third the thickness of the ribs 58, 60.

Referring also to FIG. 4, the conductive strips 47c, 47d are deposited on upper and lower faces 62, 64 of the central portion 56. The thickness of each of the conductive strips 47a–47d is approximately 1/100th the thickness of the central portion 56. The conductive strips 47 may be of a suitable conductive material, such as gold. It should be noted that the thickness of the conductive strips 47a–47d is exaggerated in FIGS. 3 and 4 for purposes of clarity.

The rib 58 includes a pair of faces 58a, 58b which are located at substantially equal distances from the faces 62, 64, respectively, of the central portion 56. Similarly, the rib 60 has a pair of faces 60a, 60b which are also disposed at substantially equal distances from the faces 62, 64, respectively.

The thickness of the ribs 58, 60 is less that one-tenth the thickness of the mounting base 32 and the paddle 30. The thickness of the ribs 58, 60 primarily determines the spring rate for the flexure 12 and provides the primary strength for the cantilever mounting construction.

Each section 50, 52 is approximately as wide as it is long, and the width or length thereof is approximately 50 times larger than the thickness of the ribs 58, 60. A list of the various dimensions for the preferred embodiment of the invention, along with the reference letters used in FIGS. 3 and 4, and description is set out below:

| Reference Letter | Dimensions (in inches unless noted otherwise) | |
| --- | --- | --- |
| A | Width of section 50 or 52 | 0.100 |
| B | Width of ribs 58, 60 | 0.025 |
| C | Width of central portion 56 | 0.050 |
| D | Thickness of ribs 58, 60 | 0.002 |
| E | Thickness of central portion 56 | 0.0005 |
| F | Width of conductive strips 47 | 0.045 |

| Reference Letter | Dimensions (in inches unless noted otherwise) | |
| --- | --- | --- |
| G | Thickness of conductive strips 47 | 1400 angstroms |
| H | Thickness of paddle 30 and mounting ring 32 | 0.0285 |
| J | Length of flexure 12 | 0.100 |

Although the ribs 58, 60 are illustrated as having planar inside walls perpendicular to the faces of the central portion 56, such as wells 58c and 58d or rib 58, it should be understood that these surfaces may alternatively be beveled or be of a curved configuration having a small radius. Moreover, the flexure sections may be beveled or curved in the region of their juncture with the paddle 30 and the mounting ring 32 to provide for a smooth transition therebetween as opposed to the abrupt transition shown in the figures.

By providing a thin central portion 56, and a pair of relatively thick ribs 58, 60, stress effects due to the conductive strips 47 are minimized, while at the same time a desired spring rate for the flexure 12 is substantially determined by the ribs 58, 60. Consequently, less sacrifice is required in the desired flexure strength in order to reduce errors due to stress effects, and, hence, proper instrument ruggedness is maintained, while bias errors caused by the conductive coating are reduced significantly. Also, it is desirable to place the conductive strips 47 such that they are located equidistant from each side of the neutral bending axis or plane of the flexure. The "neutral bending plane" is defined as that plane which does not experience tension or compression when the flexure is curved.

The embodiment disclosed in FIGS. 2-4 may be modified by eliminating the aperture 54 such that a single rib separates the central portions of the sections 50 and 52.

Figure 5:
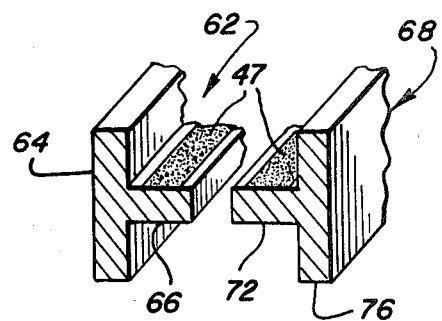
FIG. 5 is a sectional perspective view of an alternate flexure configuration.

Another embodiment of the invention is illustrated in FIG. 5 wherein a flexure 62 is configured with a rib portion 64 and a thin planar member 66 upon which the conductive material or strips 47 are deposited. Flexures of the type 62 shown in FIG. 5 can be combined to provide a bifilar flexure configuration of the type shown in FIG. 1 wherein a second flexure 68 having a rib portion 70 and a thin planar member 72 is combined with flexure 62.

Such a combined flexure approach may be desirable under certain circumstances in order to modify the response to loads tending to buckle the flexure. Alternatively, the flexure 12 could consist of a series of thin central portions, each of which is separated from adjoining central portions by a relatively thick rib. This multiple rib structure would tend to reduce buckling near the center of the flexure. Additionally flexures of this type need not have parallel surfaces, but could be for example tapered towards the force sensing element to produce a constant strength flexure.

It should also be noted that the approach described above for reducing the stress effect of a coating on a flexure element can be used with a flexure structure that is not necessarily the primary support of the force sensing element. Such a structure connecting a force sensing element to a mounting base would still require some structural integrity while producing minimum bias forces or moments. Additionally, it should be understood that even though the flexure structure illustrated in FIGS. 1-4 shows the thin portion 56 of the flexure configured as one piece with the thicker ribs 58 and 60, it may not be necessary for some applications of the invention to have the thin portion 56 carrying the conductive strips 47 physically connected to the support ribs 58 or 60.

I claim:

1. In a force sensing transducer having a force sensing element and a mounting base, a flexure structure connecting the force sensing element to the mounting base, comprising:
    a thin portion with oppositely facing surfaces for carrying electrical conductors, the strength of the thin portion being insufficient to afford the desired spring rate and support for said force sensing element;
    a thick rib extending continuously between the force sensing element and the mounting base, the composite structure of said thin portion and rib providing sufficient strength to afford the desired spring rate and support for said force sensing element and having a neutral bending plane substantially equidistant from the surfaces of said thin portion; and
    conductive layers on the faces of said thin portion interconnecting electrical circuit components on said force sensing element with circuits remote therefrom.

2. The flexure structure of claim 1 further including a second rib with the ribs being disposed on opposite sides of said thin portion.

3. The flexure of claim 1, wherein the thickness of the ribs is approximately 0.002 inch and the thickness of the thin portion is approximately 0.0005 inch.

4. The flexure structure of claim 1, wherein said thin portion is connected to said rib.

5. The flexure of claim 1, wherein the thickness of said rib is at least three times as thick as the thickness of said thin portion.

6. The flexure structure of claim 1, wherein said thin portion and said rib are configured out of an integral piece of material.

7. In a force sensing transducer having a force sensing element and a mounting base, a flexure structure for connecting the force sensing element to the mounting base, comprising:
    a first portion extending between the force sensing element and the mounting base configured with a surface adapted for receiving an electrically conductive material wherein said first portion is a thin planar member having a pair of faces, at least one of said faces having disposed thereon an electrically conductive material;
    a pair of rib portions located on opposite sides of said first portion each having a thickness greater than the thickness of said first portion and extending between the force sensing element and the mounting base, wherein the rib portions each have first and second faces substantially parallel to the faces of the first portion, the thickness of said first portion is less than one-third the thickness of the rib and said first portion is spaced substantially equidistant from said first and second rib faces.

8. The flexure of claim 7 wherein said electrically conductive material is located on each of said faces such that it is substantially equidistant from the neutral bending axis of the flexure.

9. In a force sensing transducer having a mounting base and a force sensitive element which has an electrical component, a flexure structure for securing the element to the mounting base, comprising:

a central portion extending between said element and said mounting base having a pair of faces;

at least one rib disposed adjacent to said central portion, said rib extending continuously between the force sensitive element and the mounting base and having a thickness greater than the thickness of said central portion; and an electrically conductive coating on at least one of said faces and extending between said element and said mounting base.

10. The flexure of claim 9 including two of said ribs disposed adjacent and on opposite sides of said central portion with both of said ribs having a thickness greater than said central portion.

11. The flexure of claim 10, wherein the thickness of said electrically conductive coating is approximately one hundredth the thickness of said central portion.

12. In a force sensing transducer having a mounting base and a force sensitive element which has an electrical component, a flexure structure for securing the element to the mounting base, comprising:

a central portion extending between said element and said mounting base having a pair of faces;

two ribs disposed adjacent to said central portion on opposite sides thereof with both of said ribs having a thickness greater than said central portion, wherein the ribs each have first and second faces substantially parallel to said faces of said central portion, and wherein the thickness of said central portion is less than one-third the thickness of said ribs, said central portion being spaced substantially equidistant from said first and second rib faces; and an electrically conductive coating on at least one of said faces of the central portion and extending between said element and said mounting base.

13. The flexure of claim 12, wherein the thickness of said central portion is approximately 0.0005 inch, and the thickness of the electrically conductive coating is at least an order of magnitude smaller.

14. The flexure of claim 12, wherein the thickness of said ribs is approximately 0.002 inch and the thickness of said central portion is approximately 0.0005 inch.

15. In a force sensing transducer having a mounting base and force sensitive element which has an electrical component, a flexure structure for securing the element to the mounting base, comprising:

a central portion extending between said element and said mounting base having a pair of faces wherein the width of the central portion is on the order of one-half the length thereof;

at least one rib disposed adjacent to said central portion, said rib having a thickness greater than the thickness of said central portion; and an electrically conductive coating on at least one of said faces and extending between said element and said mounting base.

16. In a force sensing transducer having a mounting base and a force sensitive element which has an electrical component, a flexure structure for securing the element to the mounting base, comprising:

a central portion extending between said element and said mounting base having a pair of faces;

at least one rib disposed adjacent to said central portion, said rib having a thickness greater than the thickness of said central portion, wherein the width of said ribs is on the order of one-half the width of said central portion; and an electrically conductive coating on at least one of said faces and extending between said element and said mounting base.

17. In a force sensing transducer having a mounting base and a force sensitive element which has an electrical component, a flexure structure for securing the element to the mounting base, comprising:

a first central portion extending between said element and said mounting base having a pair of faces;

at least one rib disposed adjacent to said central portion, said rib having a thickness greater than the thickness of said central portion;

a second central portion disposed to the side of said rib opposite to the first central portion; and an electrically conductive coating on at least one of said faces and extending between said element and said mounting base.

18. In a force sensing transducer having a mounting base and a force sensitive element which has an electrical component, a flexure structure for securing the element to the mounting base having a neutral bending axis, comprising:

a central portion extending between said element and said mounting base having a pair of faces;

at least one rib disposed adjacent to said central portion, said rib having a thickness greater than the thickness of said central portion; and an electrically conductive coating extending between the element and the mounting base on each of said faces such that the electrically conductive coating on each face is substantially equidistant from the neutral bending axis of the flexure.

19. In a force sensing transducer having a mounting base and a force sensitive element which has an electrical component, a flexure for securing said element to said mounting base, said flexure having at least one member, comprising:

a central portion extending between said element and said mounting base having a pair of faces, the width of said central portion being substantially equal to one-half the length thereof;

a pair of ribs disposed adjacent opposite sides of said central portion, the thickness of said ribs being at least three times the thickness of said central portion; and an electrically conductive coating on at least one of said faces and extending between said element and said mounting base, the thickness of said conductive coating being approximately one hundredth the thickness of said central portion.

20. The flexure of claim 19, wherein the element, the mounting base and the flexure comprise an integral piece of fused quartz.

21. The flexure of claim 19, wherein the width of each of said ribs is approximately one-half the width of said central portion.

22. The flexure of claim 19, wherein the hinge-like member is approximately as wide as it is long.

23. The flexure of claim 19, wherein the thickness of said ribs is approximately 0.002 inch and the thickness of said central portion is approximately 0.0005 inch.

24. The flexure of claim 19, wherein the thickness of said conductive coating is approximately 1400 angstroms.

25. The flexure of claim 24, wherein the width and length of said hinge-like member is approximately 0.100 inch.

26. The flexure of claim 19, 20, 21, 22, 23, 24 or 25 wherein said electrically conductive coating is located on each of said faces such that the electrically conductive coating on each face is substantially equidistant from the neutral bending axis of the flexure.

27. In a force sensitive transducer having a force sensitive element which has an electrical component secured to a mounting base by means of a flexure, the flexure having deposited on the faces thereof an electrically conductive coating, the improvement comprising:
   a flexure configuration with each face of the flexure having a channel disposed therein extending between said element and said mounting base, said channels defining a reduced thickness central portion and at least one rib on one side thereof, said electrically conductive coatings being deposited within each of said channels.

28. The flexure of claim 27 wherein said electrically conductive coating is located on each of said faces such that the electrically conductive coating on each face is substantially equidistant from the neutral bending axis of the flexure.

29. In a force sensing transducer having a force sensing element and a mounting base, a flexure structure connecting the force sensing element to the mounting base, comprising:
   a thin planar member having a pair of faces extending between the force sensing element and the mounting base, at least one of said faces having disposed thereon an electrically conductive material; and
   at least one rib portion having a thickness greater than the thickness of said thin member between the force sensing element and the mounting base wherein the thickness of the rib portions is approximately 0.002 inch and the thickness of the thin member is approximately 0.0005 inch.

30. In a force sensing transducer having a force sensing element and mounting base, a flexure structure connecting the force sensing element to the mounting base, comprising:
   a thin planar member having a pair of faces extending between the force sensing element and the mounting base, at least one of said faces having disposed thereon an electrically conductive material; and
   a pair of rib portions located on opposite sides of said first portion, each having a thickness greater than the thickness of said first portion and extending between the force sensing element and the mounting base wherein the thickness of the rib portions is approximately 0.002 inch and the thickness of the first portion is approximately 0.0005 inch.

31. In a force sensing transducer having a force sensing element and a mounting base, a flexure structure connecting the force sensing element to the mounting base, comprising:
   a thin planar member having a pair of faces extending between the force sensing element and the mounting base, at least one of said faces having disposed thereon an electrically conductive material;
   a pair of rib portions located on opposite sides of said first portion each having a thickness greater than the thickness of said first portion and extending between the force sensing element and the mounting base, wherein the rib portions each have first and second faces substantially parallel to the faces of the first portion, the thickness of the rib portions is approximately 0.002 inch and the thickness of the first portion is approximately 0.0005 inch and said first portion is spaced substantially equidistant from said first and second rib faces.

32. In a force sensing transducer having a force sensing element and mounting base, a flexure structure connecting the force sensing element to the mounting base, comprising:
   a thin planar member having a pair of faces extending between the force sensing element and the mounting base wherein an electrically conductive material is disposed on each of said faces with said faces being substantially equidistant from the neutral bending axis of the flexure; and
   at least one rib portion having a thickness greater than the thickness of said first portion extending between the force sensing element and the mounting base.

33. The flexure structure of claim 32, wherein said rib portion includes a pair of rib portions located on opposite sides of said first portion.

* * * * *

UNITED STATES PATENT AND TRADEMARK OFFICE
CERTIFICATE OF CORRECTION

PATENT NO. : 4,441,366

DATED : April 10, 1984

INVENTOR(S) : Richard A. Hanson

It is certified that error appears in the above-identified patent and that said Letters Patent is hereby corrected as shown below:

Column 6, line 60, delete "rib" and substitute therefor --ribs--.

Column 7, line 68, delete "wherein" and substitute therefor --where--.

Signed and Sealed this

Ninth Day of October 1984

[SEAL]

Attest:

*Attesting Officer*

GERALD J. MOSSINGHOFF

*Commissioner of Patents and Trademarks*